US005604090A

United States Patent [19]
Alexander et al.

[11] Patent Number: 5,604,090
[45] Date of Patent: Feb. 18, 1997

[54] METHOD FOR INCREASING TRANSDUCTION OF CELLS BY ADENO-ASSOCIATED VIRUS VECTORS

[75] Inventors: Ian E. Alexander, Brier; David W. Russell; A. Dusty Miller, both of Seattle, all of Wash.

[73] Assignee: Fred Hutchinson Cancer Research Center, Seattle, Wash.

[21] Appl. No.: 254,312

[22] Filed: Jun. 6, 1994

[51] Int. Cl.$^6$ .............................. C12N 15/87; C12N 5/00; C12N 15/86; C12Q 1/70
[52] U.S. Cl. ........................ 435/5; 435/172.3; 424/93.2
[58] Field of Search ................ 435/172.3, 5; 424/240.2, 424/93.2

[56] References Cited

PUBLICATIONS

Alexander et al., J. Virol. 68(12):8282–8287 (1994).
Russell et al., Proc. Natl. Acad. Sci. USA 92:5719–5723 (1995).
Miller et al., "Gene transfer by retrovirus vectors occurs only in cells that are actively replicating at the time of infection" *Mol. Cell. Biol.* (1990) 10:4239–4242.
Grunhaus et al., "Adenoviruses as cloning vectors" *Seminars in Virology* (1992) 3:237–252.
Geller et al., "Infection of cultured central nervous system neurons with a defective herpes simplex virus 1 vector results in stable expression of *Escherichia coli.* β–galactosidase" *Proc. Natl. Acad. Sci. USA* (1990) 87:1149–1153.
Hermonat et al., "Use of adeno–associated virus as a mammalian DNA cloning vector: transduction of neomycin resistance into mammalian tissue culture cells" *Proc. Natl. Acad. Sci. USA* (1984) 81:6466–6470.
Lebkowski et al., "Adeno–associated virus: a vector system for efficient introduction and integration of DNA into a variety of mammalian cell types" *Mol. Cell. Biol.* (1988) 8:3988–3996.
McLaughlin et al., "Adeno–associated virus general transduction vectors: analysis of proviral structures" *J. Virol.* (1988) 62:1963–1973.
Samulski et al., "Helper–free stocks of recombinant adeno–associated viruses: normal integration does not require viral gene expression" *J. Virol.* (1989) 63:3822–3828.
Carter, "Adeno–associated virus vectors" *Curr. Biol.* (1992) 3:533–539.
Muzcyzka, "Use of adeno–associated virus as a general transduction vector for mammalian cells" *Curr. Top. Microbiol. Immunol.* (1992) 158:97–129.
Flotte et al., "Gene expression from adeno–associated virus vectors in airway epithelial cells" *Am. J. Respir. Cell Mol. Biol.* (1992) 7:349–356.
Egan et al., "Defective regulation of outwardly rectifying Cl$^-$ channels by protein kinase A corrected by insertion of CFTR" *Nature* (1992) 358:581–584.
Flotte et al., "Expression of the cystic fibrosis transmembrane conductance regulator from a novel adeno–associated virus promoter" *J. Biol. Chem.* (1993) 268:3781–3790.

Walsh et al., "Regulated high level expression of a human γ–globin gene introduced into erythroid cells by an adeno–associated virus vector" *Proc. Natl. Acad. Sci. USA* (1992) 89:7257–7261.
Flotte et al., "Stable *in vivo* expression of the cystic fibrosis transmembrane conductance regulator with an adeno–associated virus vector" *Proc. Natl. Acad. Sci. USA* (1993) 90:10613–10617.
Sambrook et al., *Molecular Cloning* (1989) Cold Spring Harbor, New York. The title page and table of contents.
Gey et al., "Tissue culture studies of the proliferative capacity of cervical carcinoma and normal epithelium" *Cancer Res.* (1952) 12:264–265.
Graham et al., "Characteristics of a human cell line transformed by DNA from human adenovirus type 5" *J. Gen. Virol.* (1977) 36:59–72.
Limon et al., "Application of long–term collagenase disaggregation for the cytogenetic analysis of human solid tumors" *Cancer Genet. Cytogent.* (1986) 23:305–313.
Palmer et al., "Efficient retrovirus–mediated transfer and expression of a human adensine deaminase gene in diploid skin fibroblasts from an adenosine deaminase–deficient human" *Proc. Natl. Sci. USA* (1987) 84:1055–1059.
Samulski et al., "Cloning of adeno–associated virus into pBR322: rescue of intact virus from the recominant plasmid in human cells" *Proc. Natl. Acad. Sci. USA* (1982) 79:2077–2081.
Weiss et al., eds *RNA Tumor Viruses* (1985) 2nd ed., Cold Spring Harbor Laboratory Press, Cold Spring Harbor, New York, p. 766. A title page and table of contents are also included herewith.
Kam et al., "Cloning, sequencing, and chromosomal localization of human term placental alkaline phosphatase cDNA" *Proc. Natl. Acad. Sci. USA* (1985) 82:8715–8719.
Reddy et al., "The genome of simian virus 40" *Science* (1978) 200:494–502.
Beck et al. "Nucleotide sequence and exact localization of the neomycin phosphotransferase gene from transposon Tn5" *Gene* (1982) 19:327–336.

(List continued on next page.)

*Primary Examiner*—Mindy Fleisher
*Assistant Examiner*—Johnny F. Railey, II
*Attorney, Agent, or Firm*—Christensen O'Connor Johnson & Kindness PLLC

[57] ABSTRACT

The invention includes methods for increasing the efficiency of transduction of cells, including non-dividing cells, by recombinant AAV vectors. The methods utilize agents that alter certain aspects of DNA metabolism, more specifically, that affect DNA synthesis and/or affect repair, that impact on maintenance of chromosomal integrity, and/or that cause damage to the cellular DNA. Agents and vectors can now also be preselected and screened for transducing ability and/or transducing agents for their effect on DNA metabolism. These agents include tritiated nucleotides such as thymidine, gamma irradiation, UV irradiation, cis-platinum, etoposide, hydroxyurea and aphidicolin.

30 Claims, 11 Drawing Sheets

OTHER PUBLICATIONS

Boissy et al., "An *Escherichia coli recBCsbcBrecF* host permits the deletion-resistant propagation of plasmid clones containing the 5'-terminal palindrome of minute virus of mice" *Gene* (1985) 35:179–185.

Ruffing et al., "Assembly of viruslike particles by recombinant structural proteins of adeno-associated virus type 2 in insect cells" *J. Virol.* (1992) 66:6922–6930.

Yakobson et al., "Replication of adeno-associated virus in synchronized cells without the addition of a helper virus" *J. Virol.* (1987) 61:972–981.

Miller et al., "Cloning of the cellular receptor for amphotropic murine retroviruses reveals homology to that for gibbon ape leukemia virus" *Proc. Natl. Acad. Sci. USA* (1994) 91:78–82.

Miller et al., "Improved retroviral vectors for gene transfer and expression" *Biotechniques* (1989) 7:980–990.

Friedrich et al., "Promoter traps in embryonic stem cells: a genetic screen to indentify and mutate developmental genes in mice" *Genes and Development.* (1991) 5:1513–1523.

Fields–Berry et al., "A recombinant retrovirus encoding alkaline phosphatase confirms clonal boundary assignment in lineage analysis of murne retina" *Proc. Natl. Sci. USA* (1992) 89:693–697.

Berger et al., "Expression of active, membrane bound human placental alkaline phosphatase by transfected simian cells" *Proc. Natl. Acad. Sci. U.S.A.* (1987) 84:4885–4889.

Berger et al., "Secreted placental alkaline phosphatase: a powerful new quantitative indicator of gene expression in eukaryotic cells" *Gene* (1988) 66:1–10.

Bradford, "A rapid and sensitive method for quantitation of microgram quantitites of protein utilizing the principle of protein–dye binding" *Anal. Biochem.* (1976) 72:248–254.

Hirt, "Selective extraction of polyoma DNA from infected mouse cell cultures" *J. Mol. Biol.* (1967) 26:365–369.

Yalkinoglu et al., "DNA amplification of adeno-associated virus as a response to cellular genotoxic stress" *Cancer Res.* (1988) 48:3124–3129.

METHOD FOR INCREASING TRANSDUCTION OF CELLS BY ADENO-ASSOCIATED VIRUS VECTORS

GOVERNMENT SUPPORT

This invention was made, in part, with government support from the National Institutes of Health under Grant Nos. HL 41212 and HL 36444. The United States Government has certain rights in this invention.

TECHNICAL FIELD

This invention relates generally to adeno-associated virus (AAV) vectors for gene transfer and, more specifically, to methods for increasing transduction of cells with recombinant adeno-associated virus (AAV) vectors.

BACKGROUND

The efficient delivery of therapeutic genes to non-dividing cells with resultant long-term stable expression remains a major goal in the development of gene therapy. None of the currently available vector systems has been shown to be capable of both efficient transduction of non-dividing cells and long term expression through stable integration of the vector genome into host cell DNA. Retroviral vectors based on Moloney murine leukemia virus, while capable of integration and stable long term expression, require cell division for efficient transduction. Miller D. G. et al., *Mol. Cell. Biol.* 10, 4239–4242 (1990). In contrast, vectors based on adenovirus and herpes simplex virus are capable of transducing non-dividing cells but do not integrate into host cell DNA with any appreciable frequency. See Grunhaus A. et al., *Seminars in Virol.* 3, 237–252 (1992); Geller A. I. et al., *Proc. Natl. Acad. Sci. U.S.A.* 87, 1194–1153 (1990). The less well characterized vectors based on the dependent parvovirus, adeno-associated virus (AAV), have been shown to integrate but their potential for transducing non-dividing cells has yet to be fully investigated. See Hermonat P. L. et al., *Proc. Natl. Acad. Sci. U.S.A.* 81, 6466–6470 (1984); Lebrowski J. S. et al., *Mol. Cell. Biol.* 8, 3988–3996 (1988); McLaughlin S. K. et al., *J. Virol.* 62, 1963–1973 (1988); and Samulski R. J. et al., *J. Virol.* 63, 3822–3828 (1989).

Adeno-associated virus (AAV) vectors are among a small number of recombinant virus vector systems which have been shown to have utility as both in vitro and in vivo gene transfer vectors (reviewed in Carter, 1992, *Curr. Opinion Biotech.* 3, 533–539 (1992); Muzcyzka, *Curr. Top. Microbiol. Immunol.* 158, 97–129) and thus are potentially of great importance for human gene therapy. AAV vectors are capable of stable DNA integration and expression in a variety of cells including cystic fibrosis (CF) bronchial and nasal epithelial cells (Flotte et al., *Am. J. Respir. Cell Mol. Biol.* 7, 349–356 (1992a)); Egan et al., *Nature,* 358, 581–584 (1992); Flotte et al., *J. Biol. Chem.* 268, 3781–3790 (1993a); Flotte et al., *Proc. Natl. Aced. Sci. U.S.A.* 90, 1613–1617 (1993b), human bone marrow-derived erythroleukemia cells (Walsh et el., *Proc. Natl. Aced. Sci. U.S.A.* 89, 7257–7261 (1992)), and several others. See also Flotte et al., *Proc. Natl. Acad. Sci. U.S.A.,* 90, 10613–10617 (1993).

We have recently demonstrated that AAV vectors preferentially transduce cells in S phase of the cell cycle. However, transduction events do occur independent of S phase at low frequency. The factors within an S phase cell that facilitate transduction by AAV vectors remain undefined but are likely to directly involve or be closely linked to DNA synthesis. Possible factors include host cell polymerases required for the conversion of the single-stranded input genomes to double-stranded molecules and/or cellular factors facilitating vector integration.

SUMMARY OF THE INVENTION

Of the viral vector systems currently available for gene transfer applications, none has been demonstrated to be capable of both efficient transduction of non-dividing cells and long term expression through stable integration into host cell DNA. We have discovered that the transduction efficiency on non-dividing cells of the integrating vector system based on adeno-associated virus (AAV) can be greatly increased by treatment with agents which affect DNA metabolism. Increased transduction, particularly of non-dividing cells, can facilitate gene transfer and is useful in many applications, including the manufacture of gene products and therapeutic applications. In addition, we have discovered that the transduction efficiency of both dividing and non-dividing cells with recombinant AAV is increased by treatment with agents that alter certain aspects of DNA metabolism, more specifically, that alter DNA synthesis, DNA repair, and/or maintenance of chromosomal and DNA strand integrity. Thus, the invention includes methods for increasing the efficiency of transduction of cells, including non-dividing cells, by recombinant AAV vectors by treatment with agents that alter DNA metabolism. Accordingly, embodiments of the invention include the following.

A method of increasing AAV transduction of a cell comprising the steps of:
 a. providing an agent that alters DNA metabolism in a cell;
 b. treating the cell with an effective level of the agent;
 c. providing a recombinant AAV vector capable of integrating into DNA within the cell; and
 d. incubating the AAV vector with the cell to allow transduction of the cell by the AAV vector.

A method of increasing AAV transduction of a cell comprising the steps of:
 a. providing an agent that causes damage to cellular DNA;
 b. treating the cell with an effective level of the damaging agent;
 c. providing a recombinant AAV vector capable of integrating into the cell; and
 d. incubating the AAV vector with the cell to allow transduction of the cell by the AAV vector.

A method of increasing AAV transduction of a cell comprising the steps of:
 a. providing an agent that interferes with cellular DNA synthesis;
 b. treating the cell with an effective level of the agent;
 c. providing a recombinant AAV vector capable of integrating into DNA within the cell; and
 d. incubating the AAV vector with the cell to allow transduction of the cell with the AAV vector.

A method of increasing AAV transduction of a cell comprising the steps of:
 a. providing an agent which disrupts chromosomal integrity;
 b. treating the cell with an effective level of the agent;
 c. providing a recombinant AAV vector capable of integrating into DNA within the cell; and
 d. incubating the AAV vector with the cell to allow transduction of the cell with the AAV vector.

A method of screening for a transduction-increasing agent of a cell population comprising the steps of:
  a. preselecting an agent that alters DNA metabolism;
  b. providing the agent;
  c. treating the cell population with the agent at a level sufficient to alter DNA metabolism;
  d. providing a recombinant AAV vector capable of integrating into DNA within the cell population;
  e. incubating the AAV vector with the cell population to allow transduction of the cell population with the AAV vector; and
  f. assaying for the level of transduction of the cell population.

DETAILED DESCRIPTION OF THE INVENTION

Figure 1:
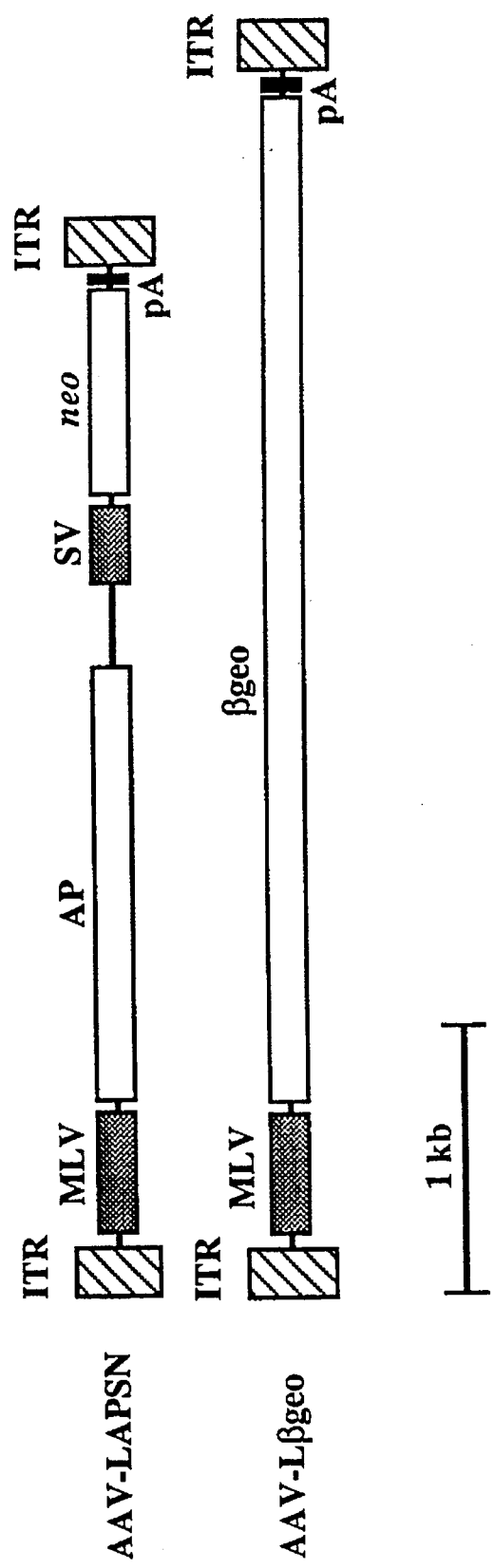
FIG. 1 is a map of AAV-LAPSN and AAV-Lβgeo vector genomes.
Figure 2A:
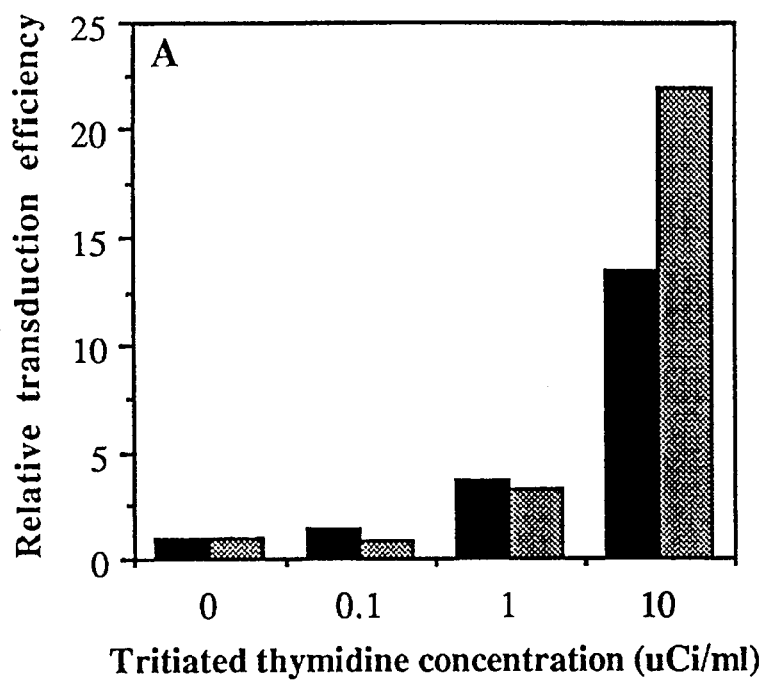
FIGS. 2A–D is comprised of four panels of bar graphs showing the effects of four agents on the transduction efficiency of AAV-LAPSN on stationary primary human fibroblast cultures: Panel A shows the effect of tritiated thymidine; Panel B shows the effect of UV irradiation exposure; Panel C shows the effect of cis-platinum; and Panel D shows the effect of exposure to gamma irradiation.
Figure 2B:
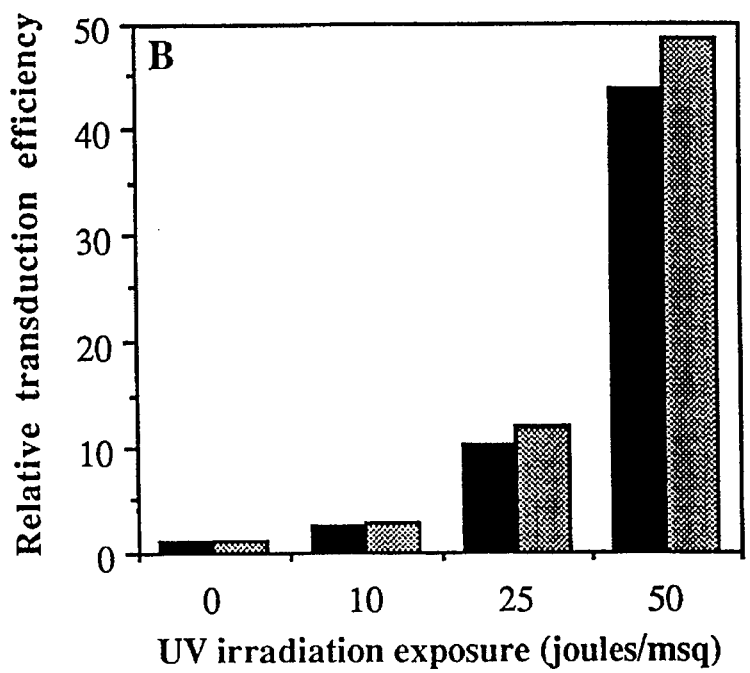
Figure 2C:
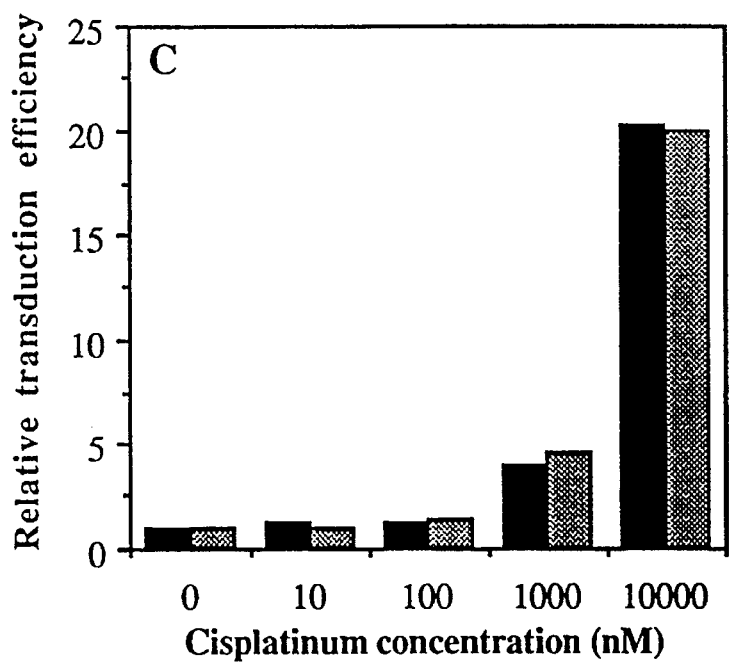
Figure 2D:
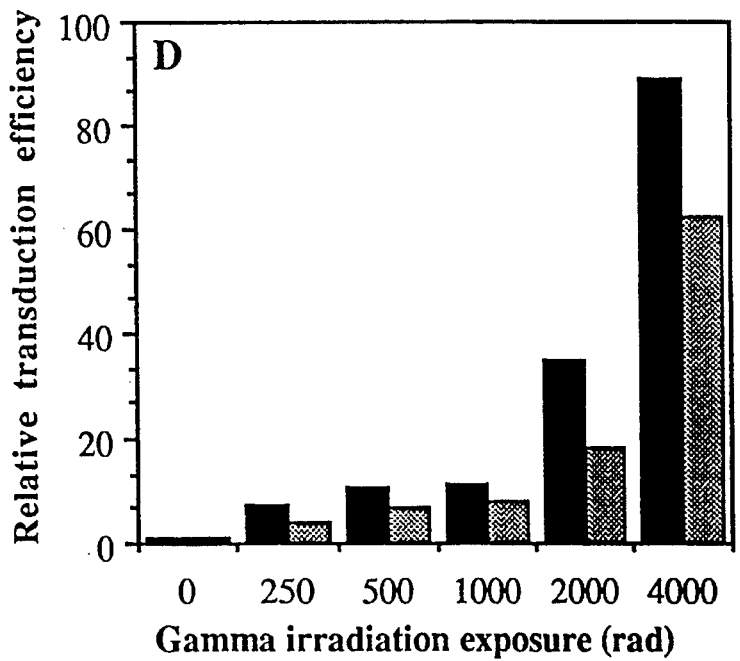

The methods of the invention, unless otherwise indicated, utilize techniques known to those in the fields of cell biology, molecular biology and gene transfer. Methods such as these are published in, for example, Muzyczka N., *Curr. Topics Microbiol. Immnunol.* 158, 97–129 (1992) and Sambrook J, et al., *Molecular Cloning,* Cold Spring Harbor Laboratory Press, Cold Spring Harbor, New York (1989).

Terms used herein are defined as follows:

The term "DNA metabolism" refers to cellular mechanisms involved in DNA repair, DNA synthesis, and/or maintenance of chromosomal and DNA strand integrity.

The term "agent altering DNA metabolism" refers to an agent that alters cellular DNA metabolism, and includes agents which cause structural DNA damage and/or loss of chromosomal integrity at the molecular, macromolecular, strand and chromosomal levels, those which alter DNA repair, and/or those which alter DNA synthesis.

The term "non-dividing cell" refers to a cell not passing through the cell cycle, specifically not the S or M phases.

The term "stationary culture" refers to conditions of cell culture under which only a minimal percentage of the cells, e.g. generally about 4%, are undergoing replication.

The term "recombinant AAV vector" refers to a vector derived from AAV that is capable of insertion into DNA, and that contains a heterologous sequence of polynucleotide operably-linked to one or more control sequences that allow its transcription.

The term "transduction" refers to the vital transfer of genetic material and its expression in a recipient cell.

The term "effective level" of agent refers to an amount or dosage of agent which, used in accord with other methods of the invention, causes an increase in transduction of a cell or cell population over a nontreated cell or cell population transduced under similar conditions (i.e. over control levels). Generally speaking this will be a level which alters DNA metabolism as herein defined.

The term "equivalent analog" of an agent refers to an agent which has the same or similar mechanisms of action on DNA metabolism as the agent to which it is an analog, and which causes an increase in transduction by AAV vectors. In the case of chemical agents, this would include structural analogs which have the same or similar effects on DNA metabolism as herein defined. Equivalent analogs also include various forms of radiation having mechanisms of action similar to ultraviolet and gamma radiation.

The present invention provides methods for increasing transduction of cells, including non-dividing cells by AAV recombinant vectors through treatment of the cells with agents that alter various aspects of DNA metabolism. Treatment with these agents can result in actual structural damage to the DNA, the induction of cellular DNA repair, interference with DNA synthesis and/or disruption of chromosomal integrity in the cell. It will also be appreciated that agents which alter DNA metabolism as defined herein include those whose principal mechanism or modes of action are directed to DNA metabolism, not those whose effect is remote.

In the practice of the methods of the invention a cell or cell population is treated with an effective level of agent and exposed to AAV vector capable of integration into cellular DNA under conditions allowing infection and transduction. The agent is, as previously defined, an agent which alters DNA metabolism, i.e. alters DNA strand integrity, DNA repair, DNA synthesis and/or chromosomal integrity and any combination of the above or. It will be appreciated that treatment by the agent can occur concurrently with or pre- or post- exposure to AAV vector or in combinations thereof. It will also be appreciated that the treatment with the agent can comprise a series of treatments at various intervals, also occurring pre-, post- or during exposure to and infection by AAV vector.

DNA damaging agents of the present invention include those which cause dimerization of adjacent nucleotides, scission of at least one DNA strand, as well as alkylating agents. Such agents include radioactive molecules, including tritiated nucleotides such as thymidine (scission), ultraviolet (UV) irradiation (dimerization), gamma irradiation (scission) and cis-platinum (alkylation). It will also be appreciated that DNA damaging agents at appropriate levels will also generally induce DNA repair. Agents which damage chromosomal integrity include not only those which physically damage the DNA strands, but those which disrupt chromosomal integrity, such as topoisomerase inhibitors. A preferred agent of this class is etoposide, which has been clinically used as an oncotherapeutic as described below. Additionally, agents affecting DNA synthesis, which include ribonucleotide reductase inhibitors such as hydroxyurea, and DNA polymerase inhibitors such as aphidicolin, are suitable for use in the method of the present invention. It will also be appreciated that different agents may have more than one effect on DNA metabolism, and that more than one agent can be employed sequentially or concurrently. It will also be appreciated that both animal and human cell populations can be treated in accordance with the methods of the present invention to increase transduction by AAV vectors.

The methods of the present invention increase transduction by recombinant AAV vectors and thus expression of the transferred genetic material. Thus the methods described herein can be utilized to increase levels of production of a desired gene product or protein in cell culture. Increased transduction is particularly useful in populations of terminally differentiated or non-dividing cells such as hematopoietic stem cells, neurons, quiescent lymphocytes and normal epithelial cells, to facilitate production of cell-specific product. It will be appreciated by those skilled in the art that any polynucleotide or gene of interest suitable for transfer via a recombinant AAV vector can be employed. Methods for recombining genetic material are well known to those skilled in the art and can be accomplished by utilizing conventional recombination technology. See Sambrook, J. et al., *Molecular Cloning*. Cold Spring Harbor Laboratory Press, Cold Spring Harbor, New York (1989). The preparation of AAV vectors carrying human therapeutic genes, such as, for example, globin genes and the cystic fibrosis transmembrane conductance regulator (CFTR) gene, can also be accomplished using approaches and recombination schemes known to or easily devised by those skilled in the art. See Walsh et al., *Proc. Natl. Aced. Sci. U.S.A.* 89, 7257–7261 (1992); and Flotte et al., *Proc. Natl. Aced. Sci. U.S.A.*, 90, 10613–10617 (1993).

In addition to the increased manufacture of a desired gene product, increased transduction in accord with the methods of the present invention provides for improved therapeutic applications of the vector. For example, in the ex vivo treatment of cell populations removed from a patient, treated with recombinant vector carrying the therapeutic gene, then reimplanted into the patient, treatment of the cell population ex vivo with transduction-increasing agents of the present invention can improve the efficacy of such treatments. With respect to in vivo or direct therapy, the patient or target site or tissue can be treated with agents of the invention to enhance transduction by the AAV recombinant vector carrying the therapeutic gene. Again this approach is particularly useful when the target cell population comprises terminally differentiated or non-dividing cells such as, for example, neuronal, hepatic and airway epithelial cells.

Further applications of the method of present invention include the screening of therapeutic genes in terminally differentiated or non-dividing cell populations by treating such cell populations ex vivo to enhance transduction, thereby allowing the testing of gene function in the cell population. Similarly, cell cycle check point genes, i.e. genes affecting cell division or the cell cycle, such as mammalian homologs of the yeast cdc genes, can be screened for therapeutic potential. The method of the present invention is also currently being utilized to screen other vectors, such as retroviral vectors, for their ability to transduce non-dividing cells, using AAV transduction in accord with the invention as a positive control for transduction. The method of the present invention further provides an assay for agents that influence or alter nucleic acid metabolism, including DNA damage, DNA repair, DNA synthesis and chromosomal integrity, by testing whether they increase transduction over untreated negative controls and positive controls of AAV transduction of the invention. Conversely, transduction-increasing agents can also now be preselected on the basis of their impact on nucleic acid metabolism, and then assayed for levels of increase in transduction over untreated negative controls and positive controls of transduction of the invention.

Preferred agents of the method of the present invention are those with the greatest effect on transduction and the least toxicity. It will be appreciated that this may vary depending on the application, for example whether ex vivo or in vivo. It will also be appreciated that different cell types may respond differently to different agents. One skilled in the art can thus select the appropriate agent (and dosage as described below) depending upon the intended use, weighing efficacy, toxicity and the nature of the target cell population as three major factors in the selection process. For example, etoposide has been delivered in vivo as an oncotherapeutic at the required doses with acceptable toxicities. Hydroxyurea treatment ex vivo also has no measurable toxicity at the doses used. Agents that cause less DNA damage such as hydroxyurea and etoposide, respectively, would thus be currently preferred, with etoposide preferred for in vivo use.

Dosage ranges of selected agents of the present invention which have been utilized are shown in the Figures and are preferably as follows: tritiated thymidine—from about 1 µCi/ml to at least 10 µCi/ml; UV irradiation—from about 25 to at least about 50 joules/msq; gamma irradiation from about 250 to about at least 4000 rad; etoposide from greater than 0 to about 100 µM, more preferably 3 µM or less; hydroxyurea—from about 0.40 mM to at least about 40.00 mM; and aphidicolin at about 5 µg/ml. The doses administered can, of course, vary, generally determined by the level of enhancement of transduction and expression balanced against any risk or deleterious side effect, by whether the use is ex vivo or in vivo and the factors described above. Monitoring levels of transduction and expression can also assist in selecting and adjusting the doses administered.

COMMERCIAL UTILITY

Cells or cell populations, particularly of non-dividing or terminally differentiated cells, can be treated in accordance with the present invention ex vivo or in vivo to increase their transduction by AAV recombinant vectors. As described herein, by increasing transduction of cell populations, the manufacture of specific desired proteins can be increased. Desirable products include clotting factors, globin gene products, cytokines and growth factors. Treatment to increase transduction in accord with the present invention also has therapeutic applications, improving transduction and therefore efficacy of in vivo and ex vivo treatment of patient cell populations and target tissues with recombinant AAV vectors. Other vectors can be screened for transduction effectiveness using transduction of the invention as a positive control. The methods of the invention additionally provide an assay for DNA metabolism-altering agents by measuring increases in levels of transduction by these agents. Transduction-increasing agents can also now be preselected by their effect on various aspects of DNA metabolism, then assayed for levels of transduction by employing the methods of the present invention. Ex vivo screening for function of a gene, particularly in non-dividing cells such as stationary fibroblasts or neuronal cells, can also be more easily accomplished in the appropriate cell type with increased transduction according to the methods of the invention.

EXAMPLES

The Examples presented below are provided as a further guide to the practitioner of ordinary skill in the art, and are not to be construed as limiting the invention in any way.

MATERIALS AND METHODS

The Examples provided below utilized the following methods, unless otherwise specified.

Cell culture. Hela cells and 293 cells have been described by Gey G. O. et al., *Cancer Res.* 12, 264 (1952) and Graham F. L. et al., *J. Gen. Virol.* 36, 59–72 (1977). Neonatal primary human foreskin fibroblasts were kindly provided by Dr. Christine Halbert and Dr. Theo Palmer having been isolated as described by Limon J. et al., *Cytogenet.* 23, 305–313 (1986) or Palmer, T. D. et al., *Proc. Natl. Acad. Sci. U.S.A.* 84, 1055–1059 (1987). Cells were maintained in Dulbecco's modified Eagle medium (DMEM) supplemented with 10% heat inactivated (30 min at 56 degrees C.) fetal bovine serum (FBS), 100 units/ml penicillin, 100 µg/ml streptomycin and 2.5 µg/ml amphotericin B. Cultures were grown in 10 cm dishes (Corning) at 37 degrees C. in 10% $CO_2$. Stock Hela and 293 cells were passaged weekly by treatment with trypsin (0.05%) EDTA (0.53 mM) and replated at cell densities appropriate for continuous exponential growth. Stock primary human fibroblast cultures were established from frozen stocks at passage 4 and maintained in culture by weekly passage for up to 10 additional passages. Each passage entailed a 1 in 2 split with one culture being maintained as stock and the other used for experimentation. Stationary cultures of primary human fibroblasts were prepared in 6 cm dishes (Corning) or in 6 well plates (Falcon) as described below.

Stationary cultures were prepared by changing the medium in confluent cultures to DMEM containing 5% heat-inactivated FBS and $10^{-6}$M dexamethasone, and maintaining these cultures for at least two weeks while replacing the medium every 3–4 days. Dividing cultures were prepared by treatment with trypsin and plating the cells at a density of either $2.5 \times 10^5$ cells per 35 mm well in 6 well plates (Falcon) or at $4 \times 10^5$ cells per 60 mm dish (Corning) the day before infection.

Vector construction, production and assay. The plasmid pALAPSN used to generate the AAV vector AAV-LAPSN has been described. The plasmids pTR, pTRneo, and pTRAAVneo was kindly provided by Dr. Sergei Zolotukhin and Dr. Nicholas Muzyczka, and were derived from the vector plasmid d 13-94 described by McLaughlin, S. K. et al., *J. Virol* 62, 1963–1973 (1988) pTR and pTRNEO is a vector cloning construct containing no insert or the SV40 early promoter and neomycin resistance gene (neo) respectively. pTRAAVNEO is a helper construct containing the AAV terminal repeats (Samulski R. J. et al., *Proc. Natl. Acad. Sci. U.S.A.* 79, 2077–2081 (1982)), the MLV LTR promoter (Weiss R. et al., *RNA tumor viruses.* Cold Spring Harbor Laboratory Press, Cold Spring Harbor, New York, p. 766 (1985)), the human placental alkaline phosphatase gone (Kam W. et al., *Proc. Natl. Acad. Sci. U.S.A.* 82, 8715–8719 (1985)), the SV40 early promoter (Reddy V. B. et al., *Science* 200, 494–502 (1978)), the neo gone (Beck E. et al., *Gene* 19, 327–336 (1982)) and the SV40 polyadenylation signal (see FIG. 2) (sequence available on request). Plasmids pPTRNEO and pALAPSN propagated in the bacterial stain JC8111 (Boissy R. et al., *Gene* 35, 179–185 (1985)) were used to generate vector stocks of AAV-SVNEO and AAV-LAPSN respectively as described previously by Hermonat, P. L. et al., *Proc. Natl. Acad. Sci. U.S.A.*, 81, 6466–6470 (1984). When necessary, vector stocks were concentrated as described by Ruffing M. et al., *J. Virol.* 66, 6922–6930 (1992). Based on the infectious center assay of Yakobson, B. et al., *J. Virol.* 61, 972–981 (1987), this method produced stocks with wild type virus titers at approximately 2% of vector titers. AAV vector particle numbers were determined by quantification of purified vector DNA on Southern blots probed with vectors sequences. The retroviral vector LAPSN (Miller, D. G. et al., *Proc. Natl. Acad. Sci. U.S.A.* 91, 78–82 (1994)) is analogous to the AAV vector AAV-LAPSN shown in FIG. 1 and was generated in PA317 packaging cells (PA317/LAPSN) as described by Miller, A.D. et al., *Biotechniques* 7, 980–990 (1989)).

The plasmid pALβgeo used to generate the AAV vector AAV-Lβgeo was constructed using standard molecular techniques from the plasmid PTR discussed above. PALβGEO contains the following sequences inserted in the Pst 1 site of pBR322 in the following order: the AAV2 ITR in the flip orientation (Samulski R. J. et al., *Proc. Natl. Acad. Sci. U.S.A.* 79, 2077–2081 (1982)), an Nhe I - Kpn I fragment of Moloney murine leukemia virus containing the retroviral promoter (Weiss R. et al., (eds) *RNA Tumour Viruses.* 766, Cold Spring Harbor Laboratory Press, Cold Spring Harbor, New York, (1985)), the fusion gene βgeo encoding both βgalactosidase and neomycin phosphotransferase (Friedrich G. et al., *Genes and Develop.* 5, 1513–1523 (1991), nucleotides 2613 to 2570 of SV40 containing the polyadenylation signal (Genbank accession #V10380), and the AAV2 ITR (flip orientation). The final size of the recombinant vector genome was 4781 bases i.e., 102% wild-type size. Plasmids were propagated in the bacterial strain JC8111 (Boissy R. et al., *Gene* 35, 179–185 (1985)) and vector stocks were generated as previously described above.

Analysis of alkaline phosphatase expression. Enzyme histochemistry was performed as described by Fields-Berry S.C. et al., *Proc. Natl. Acad. Sci. U.S.A.* 89, 693–697 (1992). Cell lysates for alkaline phosphatase assay were prepared essentially as described by Berger J. et al., *Proc. Natl. Acad. Sci. U.S.A.* 84, 4885–4889 (1987). Cell monolayers were washed twice with Dulbecco's phosphate buffered saline (PBS), scraped into 3 mls of homogenization buffer (10 Mm Tris. Hcl Ph 7.4, 1.0 Mm $MgCl_2$, 20 µM $ZnSO_4$) using a rubber policeman and pelleted at 1000×g for 5 min. The cell pellet was resuspended in 500 µl of homogenization buffer, sonicated briefly, mixed with 214 µl of 1-butanol and allowed to stand at room temperature for 2 hours. After brief centrifugation the lower aqueous phase was removed and incubated at 65 degrees C. for 10 minutes. Lysates were stored at −20 degrees C. until assayed. Alkaline phosphatase activity in cell lysates was determined using a spectophotmetric assay as described by Berger J. et al., *Gene* 66, 1–10 (1988). Ten to 100 µl of lysate was brought to a final volume of 100 µl with homogenization buffer and diluted with 100 µl of 2×SEAP buffer (2.0M diethanolamine Ph 8.0, 1.0 mM $MgCl_2$). Twenty µl of p-nitrophenyl phosphate (120 mM in 1×SEAP buffer) was added to initiate the assay. The OD at 405 nm was then followed as a function of time. Controls included a blank with no cell lysate and cell lysates from uninfected cultures. The protein content of each sample was determined using the method of Bradford M. M. *Anal. Biochem.* 72, 248–254 (1976).

Analysis of β-galactosidase expression. Cells were washed once with PBS, fixed in 3.4% formaldehyde in PBS, washed 3 times with PBS over 30 minutes and then stained in 5 mM $K_3Fe(CN)_6$, 5 mM $K_4Fe(CN)_6 \cdot 3H_2O$, 2 mM $MgCl_2$ and 1 mg/ml 5-bromo-4-chloro-3-indolyl β-D-galactopyranoside in PBS for 8 hours at 37 degrees C.

Physical and chemical treatments. Cells were exposed to gamma irradiation at 364 rad/minute from a $^{137}Cs$ source by using a Model M38-1 gammator (Radiation Machinery Corporation) and UV (254 nm) irradiated using a Stratalinker UV cross-linker (Stratagene) immediately before addition of vector. Thymidine [methyl-$^3$H](Dupont-NEN 82-89 Ci/mmol) was incubated with experimental cultures from the time of vector addition until analysis of alkaline phosphatase expression 48 hours later. Cultures were preincubated with cis-platinum(II)-diamine dichloride, hydroxyurea, etoposide or aphidicolin (all from Sigma) for 16 hours and then washed twice with fresh medium prior to addition of vector. Cultures were treated with nocodazole (Sigma) from 1000 fold concentrated stocks dissolved in dimethylsulfoxide. Cultures were incubated with nocodazole from 2 hours prior to vector addition until analysis of alkaline phosphatase expression 48 hours later. Cultures were treated with methotrexate (Sigma) from 100 fold concentrated stocks dissolved in 50 mM $NaHCO_3$ in standard DMEM without dialyzed FBS. Cultures were preincubated with methotrexate for 20 hours, then washed twice with fresh medium prior to vector addition.

Autoradiography. Tritium labeling and analysis of S-phase cells was performed as follows: Cultures were labeled with 10 μCi/ml $^3$H-thymidine (Dupont-NEN, 89 Ci/mmol) using dialyzed, heat-inactivated FBS. After labeling, cells were either stained or washed and cultured in the presence of 20 μM non-radioactive thymidine until staining. Cultures were first stained for alkaline phosphatase (Fields-Berry, S. C. Halliday, A. L. & Cepko, C. L. *Proc. Natl. Acad. Sci. U.S.A.* 89, 693–697 (1992)), rinsed with distilled water, treated with cold 5% trichloroacetic acid and processed for autoradiography as described by Miller, D. G. et al., *Mol. Cell. Biol.* 10, 4239–4242 (1990), then counterstained with nuclear fast red (1 mg/ml in 5% aluminum sulfate) to identify unlabeled nuclei.

DNA manipulations and analysis. AAV vector DNA was purified by the procedure of Samulski, R. J. et al., *J. Virol.* 63, 3822–3228 (1989). Isolation of episomal AAV vector DNA from stationary cultures was performed using a modification of the procedure described by Hirt B., *J. Mol. Biol.* 26, 365–369 (1967). Episomal and high molecular weight DNAs were fractionated as described by Hirt, followed by Proteinase K digestion, extraction with phenol, chloroform and butanol, and ethanol precipitation. All cultures used for DNA isolation were washed the day of the infection, and immediately prior to DNA purification, to remove extracellular vector particles. Southern blot analysis was performed using standard procedures described by Sambrook J. et al., *Molecular Cloning.* Cold Spring Harbor Laboratory Press, Cold Spring Harbor, New York (1989).

EXAMPLE 1

Effect of DNA Damaging Agents on Transduction Efficiency of AAV-LAPSN and AAV-Iβgeo The vectors AAV-LAPSN and AAV-Lβgeo are shown in the map of FIG. 1. The following Example shows that DNA damaging agents increase AAV vector transduction efficiency. Four agents were tested, ultraviolet light (254 nm), gamma irradiation, tritiated thymidine and the alkylating agent cis-platinum. The effect of each agent on transduction was determined by examining the relative number of alkaline phosphatase-positive cells in treated and untreated stationary primary human fibroblast cultures 48 hours after infection with the vector AAV-LAPSN. This vector contains the human placental alkaline phosphatase gene driven by the Moloney murine leukemia virus LTR promoter and the neo gene driven by the SV40 early promoter. The results are summarized in FIG. 2.

FIG. 2 is comprised of four panels of bar graphs showing the effects of four agents on the transduction efficiency of AAV-LAPSN on stationary primary human fibroblast cultures. Panel A shows the effect of tritiated thymidine; Panel B shows the effect of UV irradiation at 254 nm; Panel C shows the effect of cis-platinum; and Panel D shows the effect of exposure to gamma irradiation. Dark and light shading indicates data from two independent experiments. The fold increase in transduction efficiency was calculated by dividing the number of alkaline phosphatase-positive cells in treated cultures by the number present in untreated cultures.

As seen from the results, each agent markedly increased the transduction efficiency of AAV-LAPSN. At the maximum doses tested the increase ranged from 20 to 90 fold.

Figure 3:
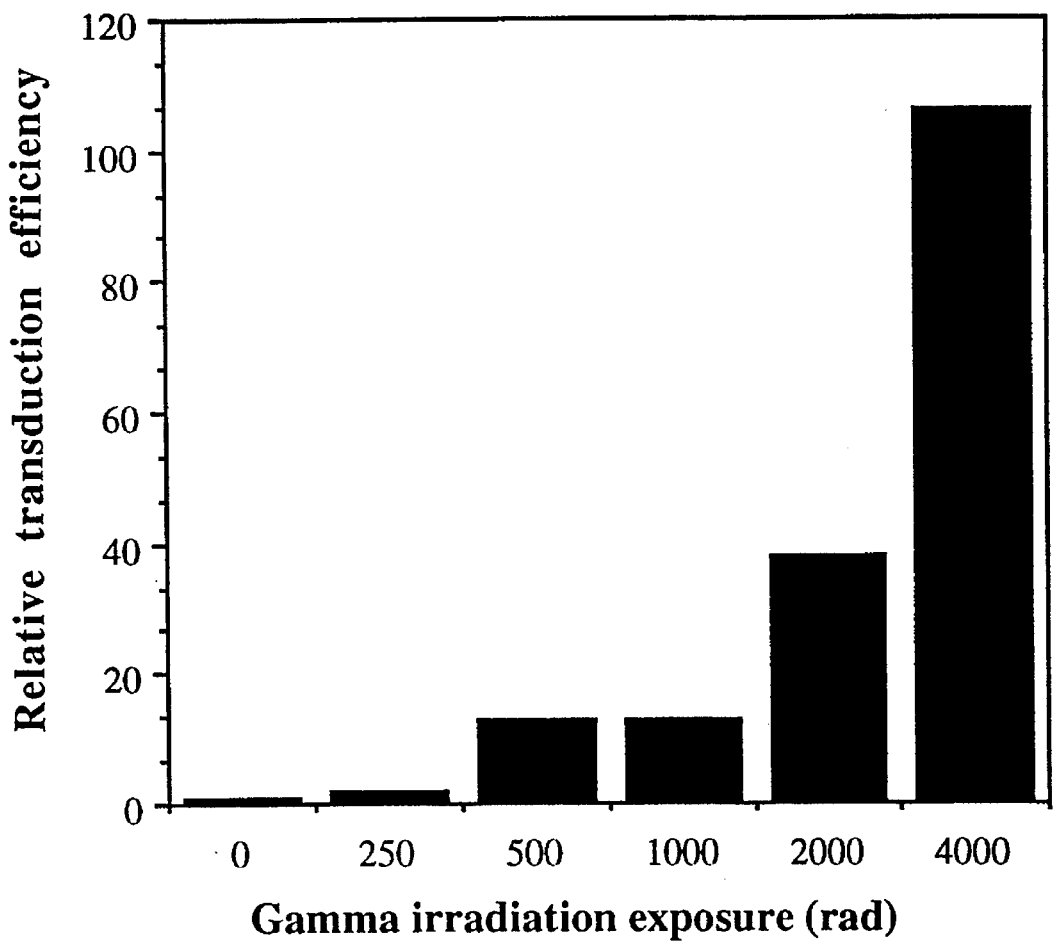
FIG. 3 is a graph illustrating the increase in transduction efficiency of AAV-Lβgeo treated with gamma irradiation.

In a separate study, gamma irradiation also increased the transduction efficiency of a second vector, AAV-Lβgeo. AAV-LAPSN contains the Moloney murine leukemia virus promoter (MLV) (Weiss R. et al., (eds) *RNA Tumour Viruses.* p. 766, Cold Spring Harbor Laboratory Press, Cold Spring Harbor, New York (1985), the human placental alkaline phosphatase gene (AP) (Kam W. et al., *Proc. Natl. Acad. Sci. U.S.A.* 82, 8715–8719 (1985), the SV40 early promoter (SV) (Reddy V. B. et al., *Science* 200, 494–502 (1978), and the neomycin phosphotransferase gene (neo) (Beck E. et al., *Gene* 19, 327–336 (1982). AAV-Lβgeo contains the MLV promoter and the fusion gene βgeo encoding both β-galactosidase and neomycin phosphotransferase activities (Friedrich G. et al., *Genes and Develop.* 5, 1513–1523 (1991)). The position of the inverted terminal repeat sequences (ITR) and the polyadenylation signal (pA) are indicated. Data generated using the vector AAV-Lβgeo is shown in FIG. 3, demonstrating that the transduction efficiency of a second AAV vector using a different reporter gene is also increased by gamma irradiation.

EXAMPLE 2

Effect of Nocodazole and Methotrexate on Transduction Efficiency of AAV-LAPSN

Two cytotoxic agents that do not directly damage DNA were tested using cells and vectors described in Example 1. The cytotoxic agents were nocodazole, an inhibitor of mitotic spindle formation and methotrexate, a folic acid antagonist. At nocodazole concentrations ranging from 50 ng/ml to 1 μg/ml, all of which produced mitotic arrest, there was little or no effect on transduction efficiency. Similarly methotrexate had no effect on transduction efficiency over the concentration range $10^{-4}$ to $10^{-9}$ molar. The failure of nocodazole to block transduction is also consistent with our earlier conclusion that mitosis is not required for transduction by AAV vectors.

EXAMPLE 3

Stability of the Transduced Reporter Gene

Figure 4:
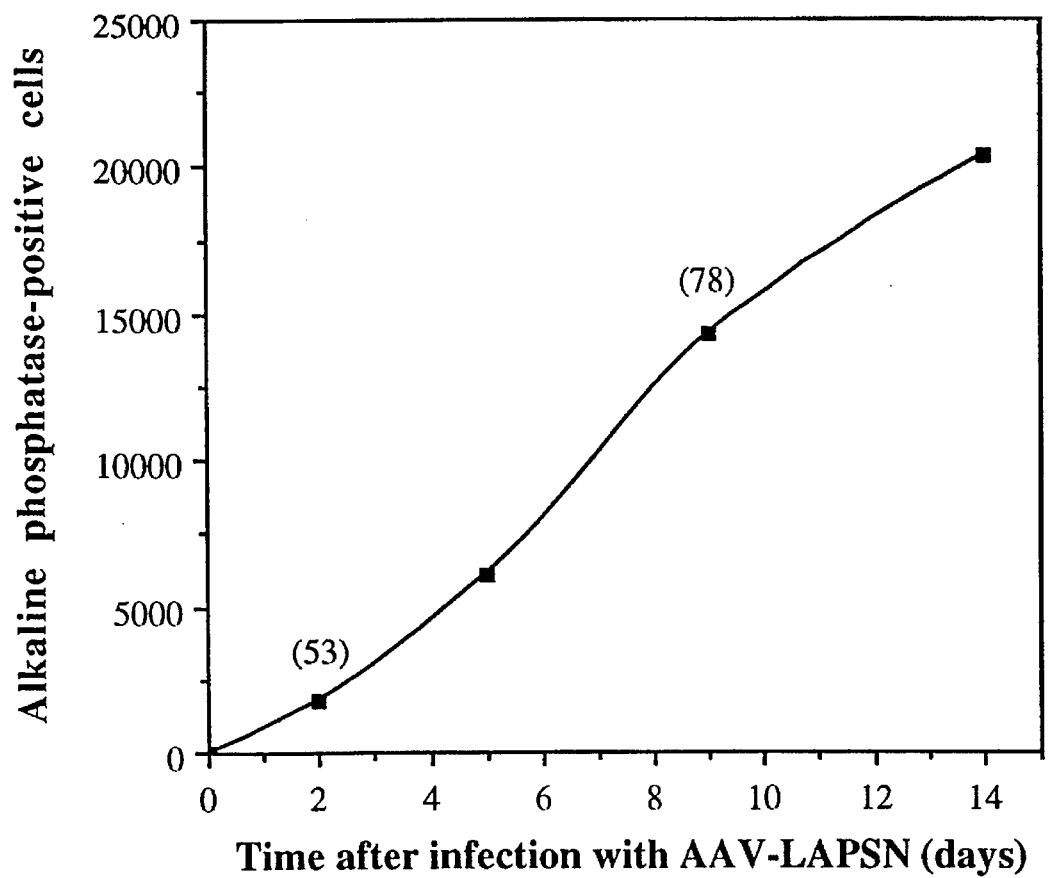
FIG. 4 is a graph showing the number of alkaline phosphatase-positive cells with time after infection with AAV-LAPSN.

The absolute number of alkaline phosphatase-positive cells in gamma irradiated (4000 rad) stationary primary human fibroblast cultures was followed for 14 days after infection with AAV-LAPSN. FIG. 4 is a graph showing the number of alkaline phosphatase-positive cells with time after infection with AAV-LAPSN. The numbers in parentheses represent the fold increase in transductants in irradiated cultures above control in unirradiated cultures at 2 and 9 days post-infection.

During the 14 day period the absolute number of alkaline phosphatase-positive cells increased 11 fold between 2 and 14 days post-infection. The fold increase in transductants in irradiated cultures above control levels in unirradiated cultures was 53 and 78 fold at 2 and 9 days post-infection respectively.

EXAMPLE 4

Increased Transduction of Dividing and Non-Dividing Cells by Tritiated Thymidine In the two independent cultures treated with 10 microcuries/ml (µCi/ml) of tritiated thymidine (FIG. 2, panel A) it was possible to determine which of the alkaline phosphatase-positive cells had been transduced independent of both S phase and mitosis by coating the stained monolayers with nuclear emulsion and performing autoradiography as described above. Double labeled cells represent the population that were in S phase at some point during the period in which transduction occurred (S phase transductants). Cells labeled with alkaline phosphatase alone represent the population of cells that were transduced independent of S phase (non-S phase transductants).

Using this technique we were able to determine that in these two cultures 10% of transduction events had occurred independent of both S phase and mitosis. Since the presence of 10 µCi/ml of tritiated thymidine in these cultures caused a mean increase in transduction efficiency of 18 fold, the absolute number of transduction events occurring independent of both S phase and mitosis exceeded the total number of transduction events occurring in control cultures that did not receive tritiated thymidine (10% of 18 is greater than 1). This result demonstrates that the presence of tritiated thymidine in the cultures had increased the transduction efficiency of non-dividing cells. However, because tritiated thymidine increases the transduction of non-S phase cells, the magnitude of the increase in non-dividing cell transduction cannot be calculated using autoradiography.

EXAMPLE 5

Effect of DNA Damaging Agent Gamma Irradiation on the Transduction of Dividing and Non-Dividing Cells To further define the effect of DNA damaging agents on the transduction of non-dividing cells we combined autoradiography with a second agent. Cultures of stationary primary human fibroblasts were gamma irradiated with doses ranging from 250 to 4000 rad 8 hours prior to addition of 10 µCi/ml tritiated thymidine and AAV-LAPSN vector, followed by alkaline phosphatase staining and autoradiography 48 hours later. Controls included no treatment, vector alone, tritiated thymidine alone and vector with tritiated thymidine.

The 8 hour interval between irradiation and exposure to vector was employed to reduce the proportion of dividing cells in the culture. In the control culture that did not receive gamma irradiation, tritiated thymidine labeling revealed that 6% of cells were in S phase at some point during the period of vector exposure, while less than 2% of cells in the culture receiving 4000 rad were in S phase at some point during the same period. Lower doses of irradiation gave intermediate values.

Figure 5:
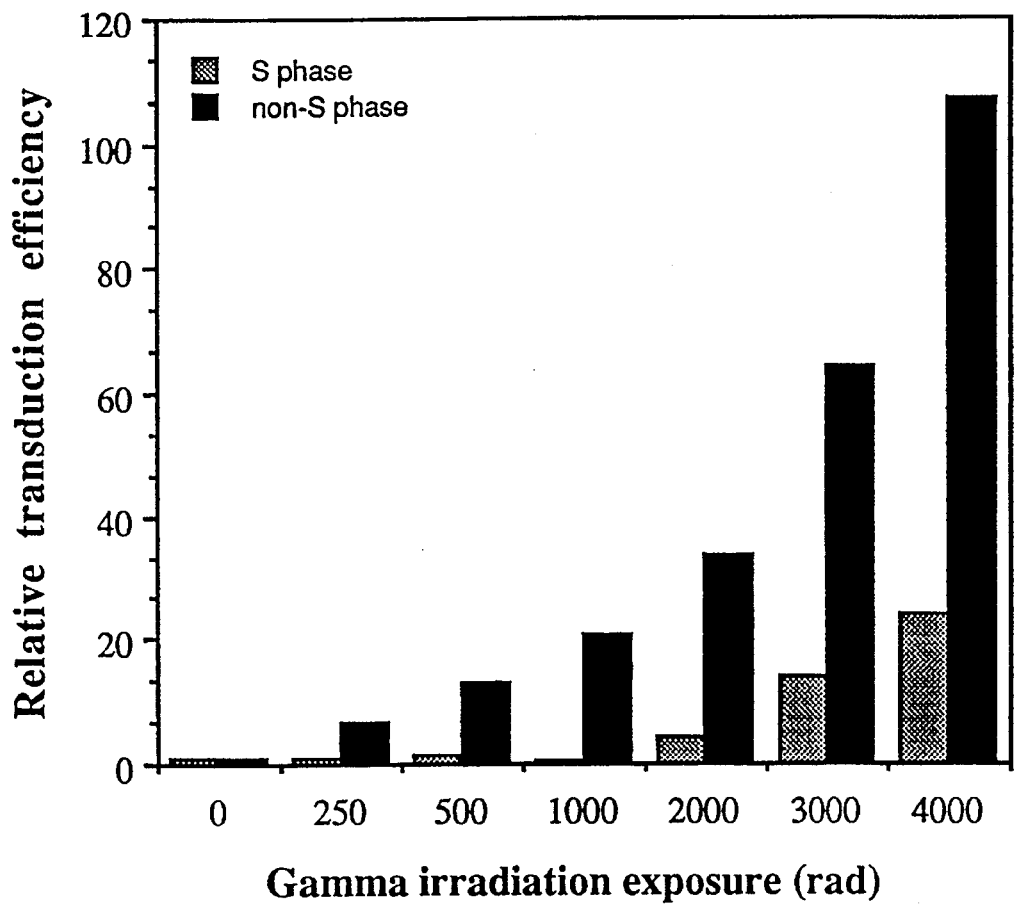
FIG. 5 is a bar graph showing the relative transduction efficiency of S phase and non-S phase cells as a result of exposure to gamma irradiation.

The fold increase in S and non-S phase transductants with increasing doses of gamma irradiation is shown in FIG. 5. The increase in transduction efficiency of non-S phase cells ranged from 7 fold at 250 rad to in excess of 100 fold at 4000 rad. The effect of irradiation on the transduction efficiency of S phase cells was much less marked and was only apparent at radiation doses of 2000 rad and above. If these data are recalculated, using values obtained from a control culture receiving no tritiated thymidine, increases in transduction efficiencies up to 750 fold are obtained for non-S phase cells. These higher fold increases in transduction efficiency represent the combined effect of tritiated thymidine and gamma irradiation and are based on the assumption that 10% of the transduction events in the control culture occurred independent of S phase. This value is based on our previous work and is likely to be an overestimate.

EXAMPLE 6

Comparison of Expression of Alkaline Phosphatase from Gamma Irradiated and Non-Irradiated Fibroblasts In order to eliminate the possibility that the results described in the Examples above resulted from increased expression rather than increased transduction, the following study was performed. Polyclonal cultures of G418-selected primary human fibroblasts transduced with AAV-LAPSN were exposed to 4000 rad of gamma irradiation and 48 hours later the alkaline phosphatase expression was compared to unirradiated cultures. One culture from each treatment group was fixed and stained for alkaline phosphatase and the alkaline phosphatase activities in cell lysates were determined for 2 cultures. There was no difference in the number of cells expressing alkaline phosphatase in irradiated and unirradiated cultures.

Figure 6:
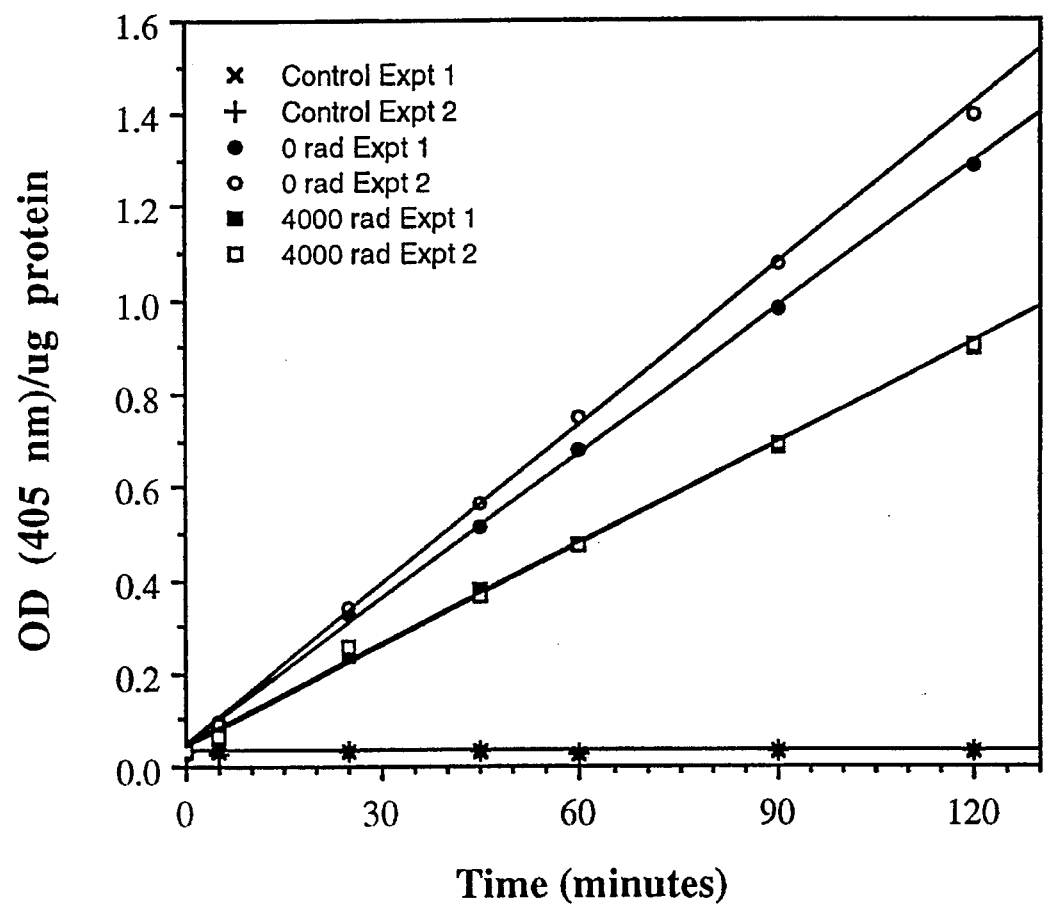
FIG. 6 is a graph showing the effect of gamma irradiation on alkaline phosphatase expression from a G418 selected polyclonal population of primary human fibroblasts transduced with AAV-LAPSN.

FIG. 6 is a graph showing the effect of gamma irradiation on alkaline phosphatase expression from the G418 selected polyclonal population of primary human fibroblasts transduced with AAV-LAPSN. Data from replicate cultures in each treatment group are shown: control naive primary human fibroblasts, transduced unirradiated fibroblasts and transduced fibroblasts 48 hours after 4000 rads of gamma irradiation.

Quantitative analysis of alkaline phosphatase activity revealed that irradiation caused a modest fall in alkaline phosphatase expression (FIG. 6). These data are consistent with the conclusion that the increased transduction efficiency of AAV-LAPSN following irradiation is not due to increased expression from transductants expressing alkaline phosphatase activity at levels not detectable by the histological staining method used.

EXAMPLE 7

Assessment of Episomal Vector DNA Amplification

The following study demonstrated that episomal vector DNA amplification does not explain increased transduction. Helper virus-independent amplification of wild-type adeno-associated virus DNA has been reported to occur following genotoxic stress (Yalkinoglu A. O. et al., *Cancer Res.* 48, 3124–3129 (1988)). More than 400 fold amplification has been observed in CHO-K1 cells following treatment with the mutagen N-methyl-N'-nitro-N-nitrosoguanidine (MNNG) and a 30 fold amplification in human diploid fibroblasts (E6). To determine whether a similar phenomena might accompany the increased transduction efficiency of AAV vectors in cells exposed to DNA damaging agents we examined Hirt supernatants from both irradiated and unirradiated cultures of stationary primary human fibroblasts 48 hours following vector exposure. Quadruplicate cultures received either no treatment, vector alone or both 4000 rad of gamma irradiation and vector. At 48 hours low molecular weight DNA was isolated from triplicate cultures in each treatment group. The fourth culture in each group was stained for alkaline phosphatase-positive cells to determine the increase in transduction efficiency caused by the gamma irradiation, which was in excess of 100 fold. An autoradiograph of low molecular weight DNA isolated from triplicate stationary cultures of primary human fibroblasts in each of three treatment groups was made. The groups were control uninfected cultures, unirradiated cultures infected with AAV-LAPSN and cultures infected with AAV-LAPSN after 4000 rads of gamma irradiation. DNA was harvested 48 hours after infection. Southern analysis used a neo probe of Hirt supernatant DNA from the triplicate cultures in each treatment group. A phosphoimager was used to quantitate the total hybridization signal in each lane and the signal representing the single stranded monomer forms of vector DNA. The maximum variation between lanes was 45% i.e., within experimental error. The results revealed no evidence of significant DNA amplification in gamma irradiated cultures. These data demonstrated that the increased transduction efficiency of AAV vectors in irradiated cells was not due to marked amplification of episomal vector DNA.

EXAMPLE 8

Measurement of Cytotoxicity of Gamma Irradiation

Figure 7:
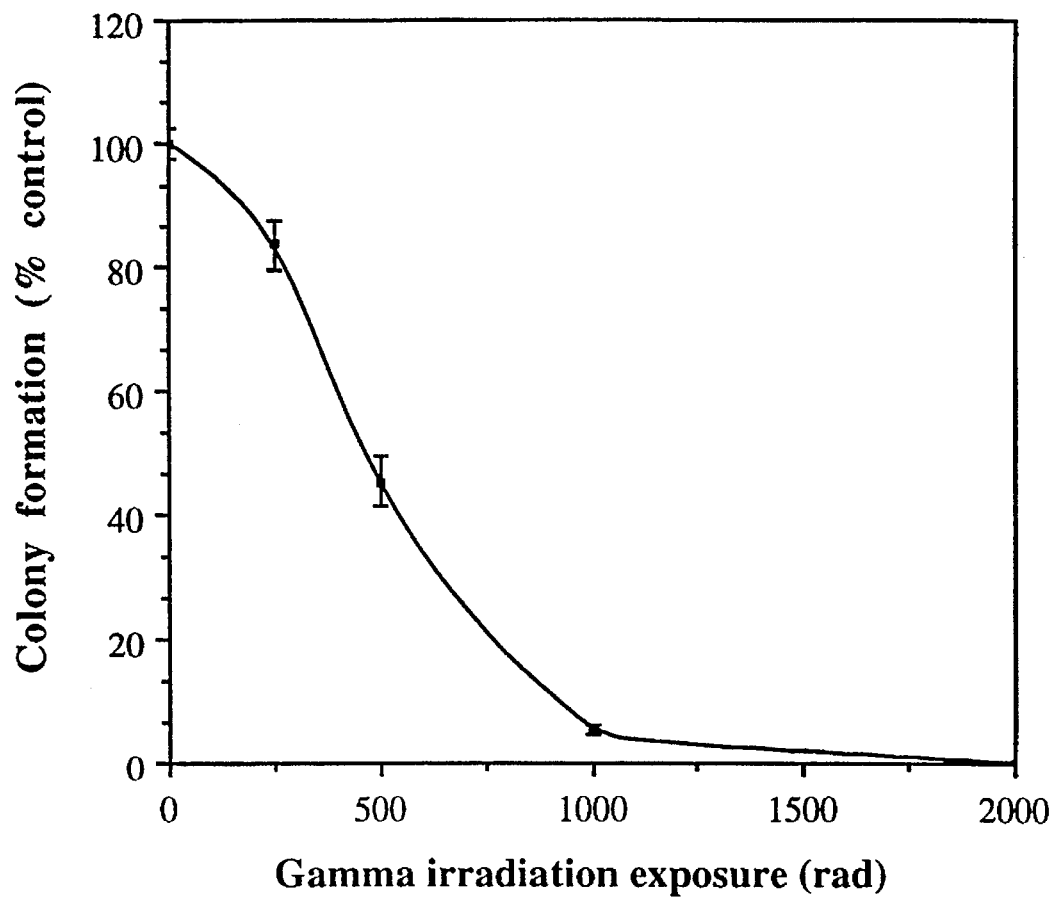
FIG. 7 is a graph showing the effect of gamma irradiation on colony formation of primary human fibroblasts.

The ability of primary human fibroblasts to form colonies following gamma irradiation was examined to determine if increased transduction occurs at radiation doses that could be applied clinically, particularly in vivo. Stationary cultures of primary human fibroblasts were exposed to gamma radiation over the dose range 250 to 4000 rad. Twenty-four hours after irradiation cultures were treated with trypsin and replated at low density. After a further 8 days colonies were fixed, stained with Coomassie blue and counted. FIG. 5 is a graph showing the effect of gamma irradiation on colony formation of primary human fibroblasts. The cells were irradiated in stationary monolayers. Error bars show SEM, n=3. As seen from FIG. 7, the gamma irradiation dose that reduced colony formation to approximately 50% of control levels was 450 rad. Nine days post-irradiation there was no appreciable difference in the viability of cells receiving 4000 rad and unirradiated cells as determined by trypan blue exclusion.

EXAMPLE 9

Effect of Hydroxyurea on Transduction of Cells by AAV-LAPSN

Figure 8A:
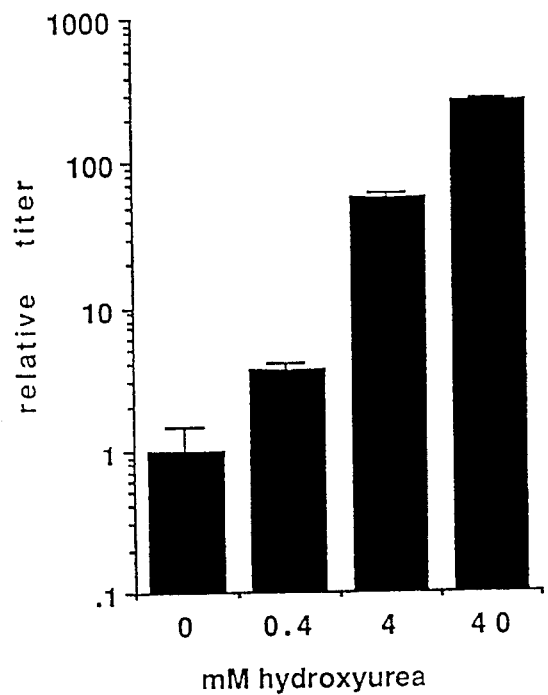
FIGS. 8A–C contains three panels of bar graphs showing the effect of hydroxyurea on titers of AAV-LAPSN in transduced stationary fibroblast cultures. Panel A shows the effect on stationary titers; Panel B shows the effect on dividing titers; and Panel C shows a comparison of the effect on stationary and dividing cultures.
Figure 8B:
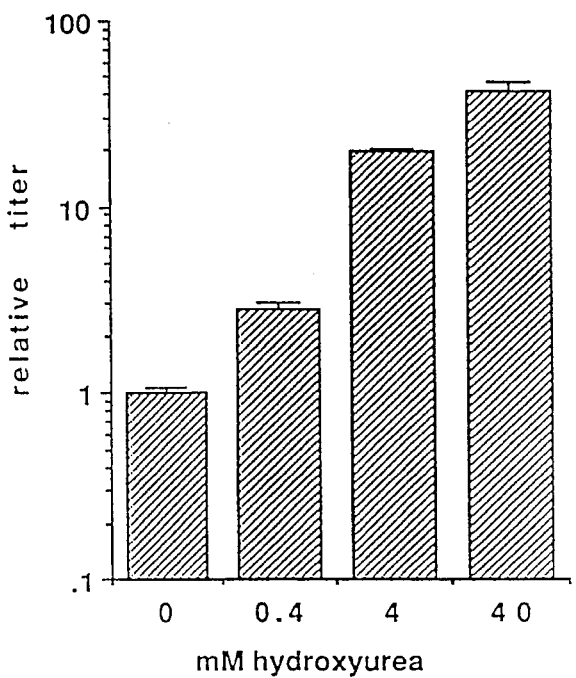
Figure 8C:
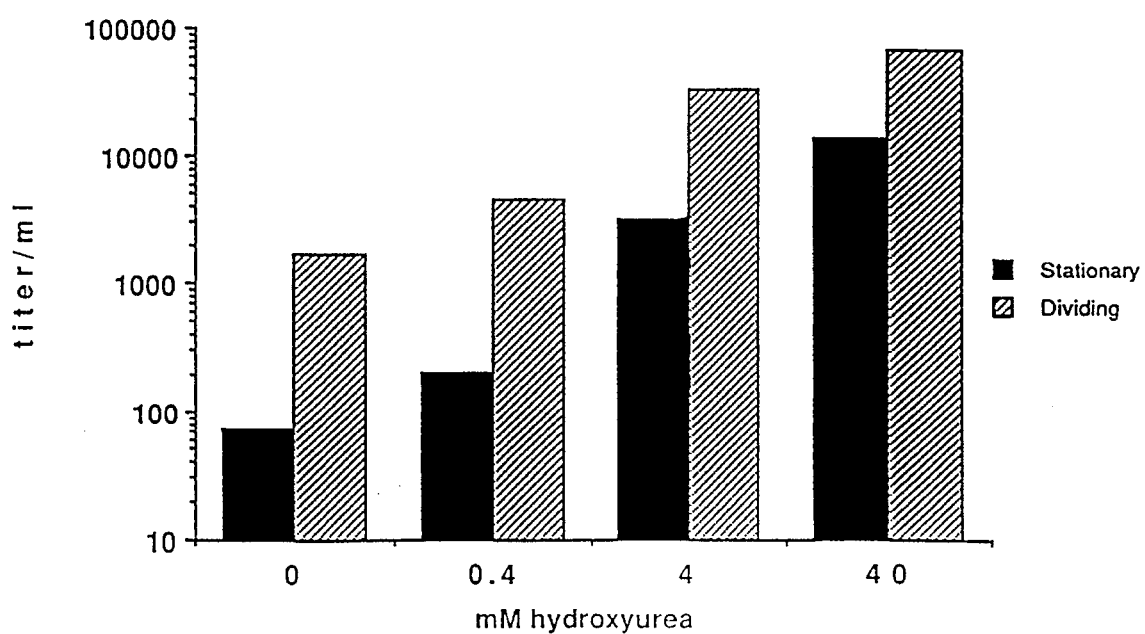

Dividing and stationary primary human fibroblast cultures were prepared as described above. Cultures were pretreated with hydroxyurea at the indicated concentrations for 16 hours, washed twice with fresh medium, then exposed to AAV-LAPSN vector stocks. Straining for alkaline phosphates was performed 48 hours later. Experiments were performed in triplicate and relative titers are the number of cell foci expressing alkaline phosphatase in treated cultures as compared to control untreated cultures (shown as mean with standard error bars in FIG. 8). Referring to FIG. 8, the top left graph shows the results on stationary cultures, the top right graph shows the results on dividing cultures, and the bottom graph shows compares the results using the absolute vector titer (alkaline phosphatase foci forming units/ml).

EXAMPLE 10

Effect of Hydroxyurea on Stationary Human Fibroblast Viability

Stationary human fibroblast cultures were exposed to hydroxyurea at the indicated concentration as in FIG. 8, then treated with trypsin, plated at different dilutions in fresh media, allowed to proliferate until colonies were clearly visible, then the number of viable colony forming units per well (CFU/well; 6 well plate) were determined. The experiment was performed in triplicate using different concentrations of hydroxyurea as indicated in Table 1 below. Shown are the CFU/well, average CFU/well for each treatment (AVG), standard deviation (SDEV) and standard error (SE).

TABLE 1

AAV HYDROXYUREA KILL CURVE
Effect of hydroxyurea (HU) on stationary human fibroblast cell viability

| mM HU | CFU/well | AVG | SDEV | SE |
| --- | --- | --- | --- | --- |
| 0.00 | 768,000 | | | |
| 0.00 | 480,000 | | | |
| 0.00 | 592,000 | | | |
| | | 613,333 | 145,180 | 83,919 |
| 0.40 | 544,000 | | | |
| 0.40 | 576,000 | | | |
| 0.40 | 576,000 | | | |
| | | 565,333 | 18,475 | 10,679 |
| 4.00 | 448,000 | | | |
| 4.00 | 752,000 | | | |
| 4.00 | 560,000 | | | |
| | | 586,667 | 153,744 | 88,870 |
| 40.00 | 608,000 | | | |
| 40.00 | 624,000 | | | |
| 40.00 | 608,000 | | | |
| | | 613,333 | 9,238 | 5,340 |

The results shown in Table 1 above indicate that the viability of the cells was essentially unaffected by hydroxyurea within a range of about 0.40 to 40.00 mM.

EXAMPLE 11

Effect of Etoposide on Transduction by AAV

Stationary human fibroblast cultures were prepared and AAV-LAPSN stocks were titered as in FIG. 6, except that etoposide was used instead of hydroxyurea. The results of two independent experiments are shown in the bar graph of FIG. 9. Titers are relative to untreated cultures.

Figure 9:
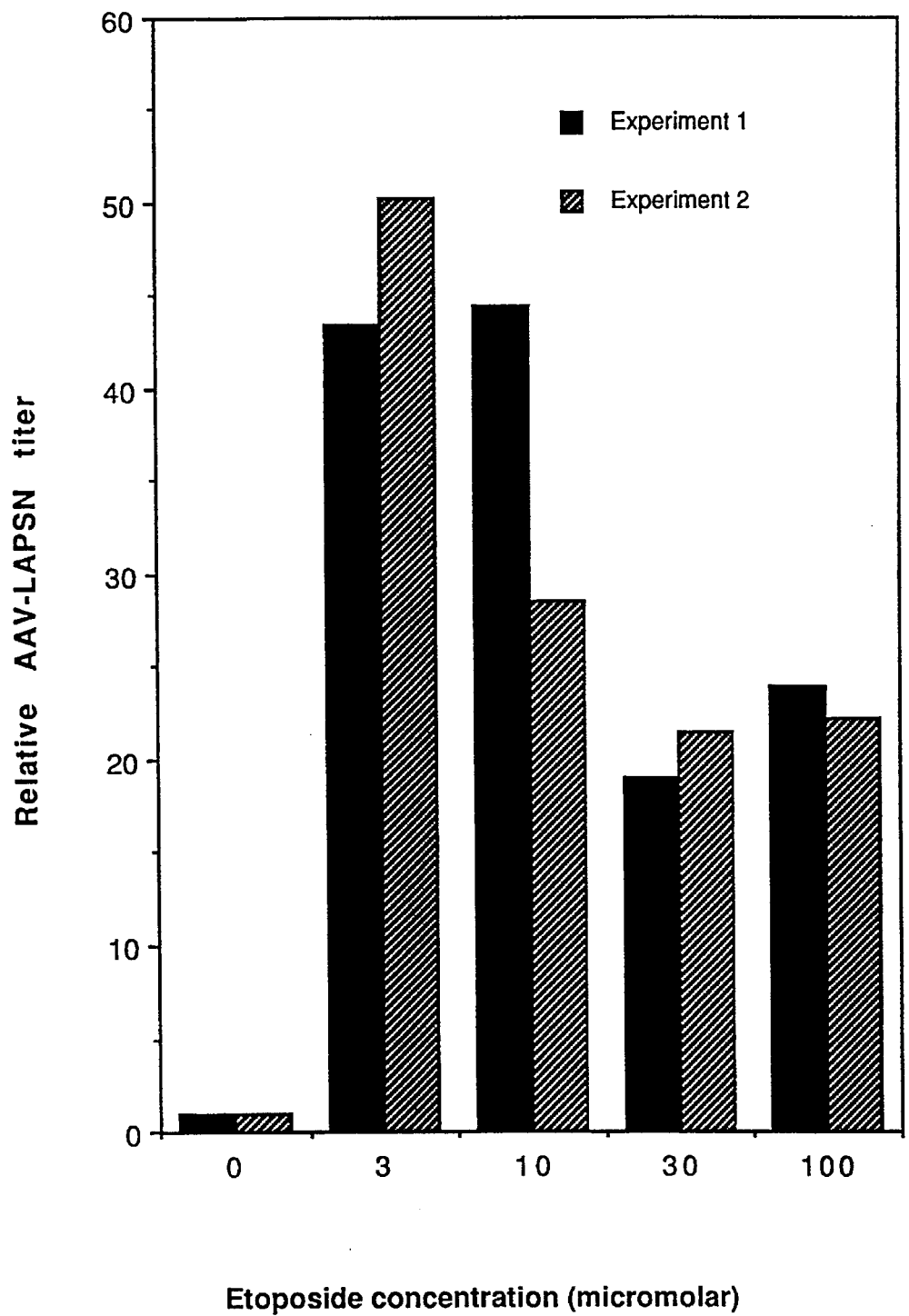
FIG. 9 is a bar graph showing the effect of etoposide on titers of AAV-LAPSN in transduced stationary fibroblast cultures.

FIG. 9 is a bar graph showing the effect of etoposide on titers of AAV-LAPSN from transduced stationary fibroblasts.

EXAMPLE 12

Effect of Aphidicolin on Transduction by AAV

Stationary human fibroblast cultures were prepared and AAV-LAPSN stocks were titered as in FIG. 6, except that aphidicolin was used instead of hydroxyurea. Aphidicolin at

EXAMPLE 13

Transduction with Therapeutic AAV Vector

A recombinant AAV vector carrying a globin gene is constructed as generally described by Walsh et al., *Proc. Natl. Acad. Sci. U.S.A.* 89, 7257–7261 (1992). Bone marrow is removed using standard bone marrow harvest techniques from a patient suffering from sickle cell anemia or thalassemia. The patient bone marrow is treated with hydroxyurea at concentrations of from 0.40 to 40.00 mM as described above. After preincubation with hydroxyurea for 16 hours, the bone marrow is exposed to the AAV recombinant vector under transducing conditions as described above. After infection the treated bone marrow is reinfused into the patient using standard reinfusion protocols. The patient is monitored for increased globin production using clinical indica of successful treatment of the underlying pathology.

We claim:

1. A method of increasing AAV transduction of a cell comprising the steps of:
   a. providing an agent that alters DNA metabolism in a cell;
   b. treating the cell with an effective level of the agent;
   c. providing a recombinant AAV vector capable of integrating into DNA within the cell; and
   d. incubating the AAV vector with the cell to allow transduction of the cell by the AAV vector.

2. A method according to claim 1 wherein treatment with the agent alters DNA structure within the cell.

3. A method according to claim 1 wherein treatment with the agent alters DNA repair within the cell.

4. A method according to claim 1 wherein treatment with the agent alters DNA synthesis within the cell.

5. A method according to claim 1 wherein treatment with the agent alters chromosomal integrity within the cell.

6. A method according to claim 2, wherein the agent is selected from the group consisting of tritiated thymidine, UV irradiation, gamma irradiation, cis-platinum and equivalent analogs thereof.

7. A method according to claim 4, wherein the agent is selected from the group consisting of hydroxyurea, aphidicolin and equivalent analogs thereof.

8. A method according to claim 5 wherein the agent is an inhibitor of topoisomerase.

9. A method according to claim 1 wherein the cell is a non-dividing cell.

10. A method of increasing AAV transduction of a cell comprising the steps of:
    a. providing an agent that causes damage to cellular DNA;
    b. treating the cell with an effective level of the damaging agent;
    c. providing a recombinant AAV vector capable of integrating into the cell; and
    d. incubating the AAV vector with the cell to allow transduction of the cell by the AAV vector.

11. A method according to claim 10 wherein the level of the agent causing damage to the cellular DNA induces a cellular DNA repair mechanism.

12. A method according to claim 10 wherein the agent causing damage to the cellular DNA causes dimerization of spatially adjacent nucleotides.

13. A method according to claim 10 wherein the agent causing damage to the cellular DNA causes scission of the DNA backbone of at least one strand of the DNA.

14. A method according to claim 10 wherein the agent causing damage to the cellular DNA is an alkylating agent.

15. A method according to claim 10 wherein the agent causing damage to the cellular DNA is a radioactive molecule.

16. A method according to claim 12 wherein the agent comprises UV irradiation.

17. A method according to claim 13 wherein the agent comprises a radioactive nucleotide.

18. A method according to claim 13 wherein the agent comprises gamma irradiation.

19. A method according to claim 14 wherein the agent comprises cis-platinum.

20. A method according to claim 16 wherein the radioactive nucleotide comprises tritiated thymidine.

21. A method according to claim 10 wherein the cell is a non-dividing cell.

22. A method of increasing AAV transduction of a cell comprising the steps of:
    a. providing an agent that interferes with cellular DNA synthesis;
    b. treating the cell with an effective level of the agent;
    c. providing a recombinant AAV vector capable of integrating into DNA within the cell; and
    d. incubating the AAV vector with the cell to allow transduction of the cell with the AAV vector.

23. A method of claim 22 wherein the agent comprises a ribonucleotide reductase inhibitor.

24. A method of claim 22 wherein the agent comprises a DNA polymerase inhibitor.

25. A method of claim 23 wherein the agent comprises hydroxyurea.

26. A method of claim 24 wherein the agent comprises aphidicolin.

27. A method of claim 22 wherein the cell is a non-dividing cell.

28. A method of increasing AAV transduction of a cell comprising the steps of:
    a. providing an agent which disrupts chromosomal integrity;
    b. treating the cell with an effective level of the agent;
    c. providing a recombinant AAV vector capable of integrating into DNA within the cell; and
    d. incubating the AAV vector with the cell to allow transduction of the cell with the AAV vector.

29. A method of claim 28 wherein the agent comprises etoposide.

30. A method of screening for a transduction-increasing agent of a cell population comprising the steps of:
    a. preselecting an agent that alters DNA metabolism;
    b. providing the agent;
    c. treating the cell population with the agent at a level sufficient to alter DNA metabolism;
    d. providing a recombinant AAV vector capable of integrating into DNA within the cell population;
    e. incubating the AAV vector with the cell population to allow transduction of the cell population with the AAV vector; and
    f. assaying for the level of transduction of the cell population, by measuring and comparing the levels of transduction observed in treated and untreated cells.

* * * * *